United States Patent
Park et al.

(10) Patent No.: US 7,396,443 B2
(45) Date of Patent: Jul. 8, 2008

(54) SOLID-STATE ELECTROCHEMICAL HYDROGEN PROBE FOR THE MEASUREMENT OF HYDROGEN CONTENT IN THE MOLTEN ALUMINUM

(76) Inventors: Dongsub Park, 126-1501 Kunmaeul, 121 Tanhyun IIsan, Goyang, Kyunggi (KR); Jungsook Hwang, 122-801 Hanbit Apt. 99 Eoun-dong, Yusong-gu, Daejeon (KR)

( * ) Notice: Subject to any disclaimer, the term of this patent is extended or adjusted under 35 U.S.C. 154(b) by 746 days.

(21) Appl. No.: 10/777,767

(22) Filed: Feb. 13, 2004

(65) Prior Publication Data

US 2005/0029100 A1 Feb. 10, 2005

(30) Foreign Application Priority Data

Feb. 17, 2003 (KR) .................. 10-2003-0009777

(51) Int. Cl.
*G01N 27/406* (2006.01)
(52) U.S. Cl. .................... 204/422; 204/423
(58) Field of Classification Search ............ 204/424, 204/427, 429, 421, 422, 423
See application file for complete search history.

(56) References Cited

U.S. PATENT DOCUMENTS

| | | | |
|---|---|---|---|
| 3,567,383 A * | 3/1971 | Langley et al. ............. | 436/3 |
| 3,864,232 A * | 2/1975 | Handman et al. ........... | 204/422 |
| 4,595,485 A * | 6/1986 | Takahashi et al. .......... | 204/406 |
| 4,882,032 A * | 11/1989 | Tiwari ........................ | 204/422 |

FOREIGN PATENT DOCUMENTS

| | | |
|---|---|---|
| JP | 4-62463 | 2/1992 |
| JP | 4-62464 | 2/1992 |
| JP | 7-20082 | 1/1995 |
| JP | 7-20083 | 1/1995 |
| JP | 7-20084 | 1/1995 |
| JP | 8-29375 | 2/1996 |
| JP | 8-29379 | 2/1996 |
| JP | 8-35947 | 2/1996 |
| JP | 10-260151 | 9/1998 |
| JP | 2000-19152 | 1/2000 |

OTHER PUBLICATIONS

Machine generated translation of JP 08-035,947, Feb. 1996.*

* cited by examiner

*Primary Examiner*—Kaj K. Olsen
(74) *Attorney, Agent, or Firm*—McKenna Long & Aldridge LLP

(57) ABSTRACT

An electrochemical gas probe capable of measuring an amount of gas in a molten metal. The probe comprises a sensing unit that includes a reference electrode, a sensing electrode, a solid-state reference mixture adjacent to the reference electrode, and a conductor between the reference electrode and a sensing electrode. The probe also comprises a supporting unit that includes a main support, a protection cover and a stabilizing material, wherein the stabilizing material is between the sensing unit and the protection cover of the supporting unit. By using a solid-state reference material, the change of hydrogen content in molten aluminum may be conveniently monitored during a degassing process.

13 Claims, 3 Drawing Sheets

US 7,396,443 B2

SOLID-STATE ELECTROCHEMICAL HYDROGEN PROBE FOR THE MEASUREMENT OF HYDROGEN CONTENT IN THE MOLTEN ALUMINUM

This application claims the benefit of Korean Patent Application No. 2003-9777, filed on Feb. 17, 2003, which is hereby incorporated by reference for all purposes as if fully set forth herein.

BACKGROUND OF THE INVENTION

1. Field of the Invention

The present invention relates to an electrochemical probe, and more particularly, to an electrochemical hydrogen probe having a solid-state reference electrode, which measures the amount of dissolved hydrogen in molten aluminum (Al).

2. Discussion of the Related Art

There are many ways of fabricating aluminum (Al) products, such as casting, forging and sintering aluminum powders. Among them, casting is the most popular and cheapest way of fabricating aluminum products. During the casting process, however, hydrogen is inevitably trapped in the aluminum products by a dissociation reaction of moisture in the air, where oxygen is captured by the aluminum to form aluminum oxide. Due to the large difference in the solubility of hydrogen between solid aluminum and liquid aluminum (hydrogen dissolves in liquid aluminum about 10 to 20 times more than in solid phase aluminum), dissolved hydrogen accumulates and forms voids or porosities in the final products. These defects can cause a reduction in mechanical strength and adversely affect the appearance of the final products. Therefore, the aluminum foundry industry generally employs a degassing process to remove hydrogen in molten aluminum. Since the amount of dissolved hydrogen depends on alloying elements and the level of humidity in the environment, the duration of the degassing process has to be changed from time to time in order to maintain a constant hydrogen level in molten aluminum, and hydrogen probes are an essential tool for the in-situ monitoring of hydrogen content in molten aluminum during the degassing process.

Conventional methods for measuring hydrogen content in molten aluminum may involve cutting final casting products to check the fraction of voids appearing in the cross-section of solidified aluminum ingots, which are formed by dissolved hydrogen, or involve analyzing the concentration of hydrogen in the gas which is equilibrated with argon (Ar) bubbled through the melt. The destructive nature of the former test gives rise to a sluggish throughput with a high cost of measurement. The latter needs a gas bubbling system, which also results in similar disadvantages as the former test. Alternatively, there exists an electrochemical method using a solid electrolyte for measuring hydrogen content in molten aluminum. However, this method uses a gas reference instead of a solid reference, which requires the use of a standard gas tank whenever measurements are made. Thus, this electrochemical method is inconvenient and it increases measurement costs due to the expense associated with the use of standard gas.

The conventional electrochemical sensors that use the principle of a concentration galvanic cell can measure oxygen content in molten steel or hydrogen content in molten aluminum. However, they also require a reference electrode that is in contact with a standard gas with a known gas concentration. For example, an oxygen probe in the steel industry uses air containing 0.21 atm-oxygen as a standard gas. In this way, the chemical potential of a detecting gas is set at the reference electrode to a constant value, whereby the measured electromotive force (EMF) becomes proportional to the gas content at the sensing electrode that is in contact with a gas to be detected.

Thus, most galvanic cell type gas sensors that include a hydrogen probe need a gas reference, which is inconvenient as a standard gas mixture is needed. Moreover, such gas sensors increase measurement costs due to the use of expensive standard gas.

Replacement of the gas reference with a solid phase mixture can solve the inconveniences arising from the conventional structure of the electrochemical hydrogen sensor of the galvanic cell structure. The adoption of such a solid-state reference can simplify the sensor structure, because it can be easily installed within the sensing element, but such problems as instability and gas leakage remain.

In the aluminum foundry industry, controlling the amount of hydrogen dissolved in molten aluminum is one of the most important quality control issues. As described above, conventional hydrogen measuring devices have problems such as large size, inconvenience of testing and high cost of maintenance.

BRIEF SUMMARY OF THE INVENTION

Accordingly, the present invention is directed to an electrochemical probe that substantially obviates one or more of the problems due to limitations and disadvantages of the prior art.

An advantage of the present invention is to provide an electrochemical probe with a solid-phase reference that has a simple structure and small in size.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, an electrochemical gas probe for measuring an amount of gas in a molten metal may, for example, include a sensing unit having a reference electrode, a sensing electrode, a solid-state reference mixture adjacent to the reference electrode, and a conductor between the reference electrode and the sensing electrode; and a supporting unit having a main support, a protection cover and a stabilizing material, wherein the stabilizing material is between the sensing unit and the protection cover of the supporting unit.

It is to be understood that both the foregoing general description and the following detailed description are exemplary and explanatory and are intended to provide further explanation of the invention as claimed.

BRIEF DESCRIPTION OF THE DRAWING

The accompanying drawings, which are included to provide a further understanding of the invention and are incorporated in and constitute a part of this application, illustrate embodiment(s) of the invention and together with the description serve to explain the principle of the invention.

In the drawings.

DETAILED DESCRIPTION OF THE ILLUSTRATED EMBODIMENT

The exemplary embodiment of the present invention are now described with reference to an exemplary electrochemical hydrogen probe capable of measuring the amount of hydrogen dissolved in molten aluminum, in accordance with the principles of the present invention.

An electrochemical hydrogen probe according to the principles of the present invention uses a solid phase reference material instead of a gas reference so that the measuring instrument has a simple structure and is small in size.

In general, solid reference materials in a closed chamber maintain a well-defined hydrogen gas pressure at operating temperatures similar to gas references. However, the solid reference materials have inherent instability problems, which require a new inventive method and structure for stabilization.

An electrochemical hydrogen probe with galvanic concentration cell structure (or hydrogen probe) according to an embodiment of the present invention uses a proton conductor that carries its currents by proton at 600-900° C. as a solid electrolyte. When there is a difference in hydrogen activity (or pressure) across the proton conductor, an electromotive force (EMF) is generated, which is proportional to the magnitude of the difference in hydrogen pressure across the electrolyte. Thus, the concentration cell with the proton conductor can be used as a hydrogen probe if the hydrogen pressure at one side of the electrolyte is fixed at a known value. It is known in thermodynamics that a mixture of metal and metal hydride can set hydrogen pressure to a well-defined value for a given temperature. This principle is adopted to provide a constant hydrogen pressure at a reference electrode of a hydrogen probe according to the principles of the present invention, with a solid reference mixture being the hydrogen source.

Figure 1:
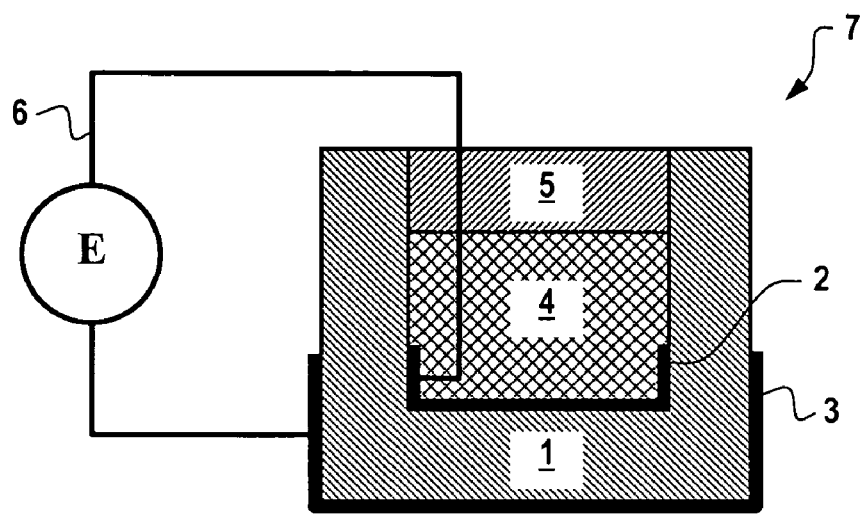
FIG. 1 is a schematic drawing illustrating the structure of a sensing unit of a hydrogen probe according to an embodiment of the present invention.

FIG. 1 is a schematic drawing illustrating the structure of a sensing unit of an electrochemical hydrogen probe according to an embodiment of the present invention. The sensing unit of the hydrogen probe includes a proton conductor 1, a reference electrode 2, a solid-state reference mixture 4 and a sensing electrode 3. Calcium zirconate doped with In, $CaZr_{1-x}In_xO_3$ (0.04<x<0.2) is used for the proton conductor 1. The solid-state reference mixture 4 at the reference electrode 2 is a mixture of Ti/TiH₂ and TiO, Zr/ZrH and ZrO₂, or Ca/CaH₂ and CaO. The solid-state reference mixture 4 is protected by a ceramic lid cover 5 sealed gas-tight with a high temperature sealing material, and Pt wires 6 are connected to the reference and sensing electrodes 2 and 3 for the connection to a measuring instrument located outside of the sensing unit.

When there is a difference in hydrogen and oxygen pressures across the proton conductor 1, an EMF arises across the electrodes 2 and 3 depending on both the difference in the oxygen pressure and the hydrogen pressure. This may be expressed as

Figure 3:
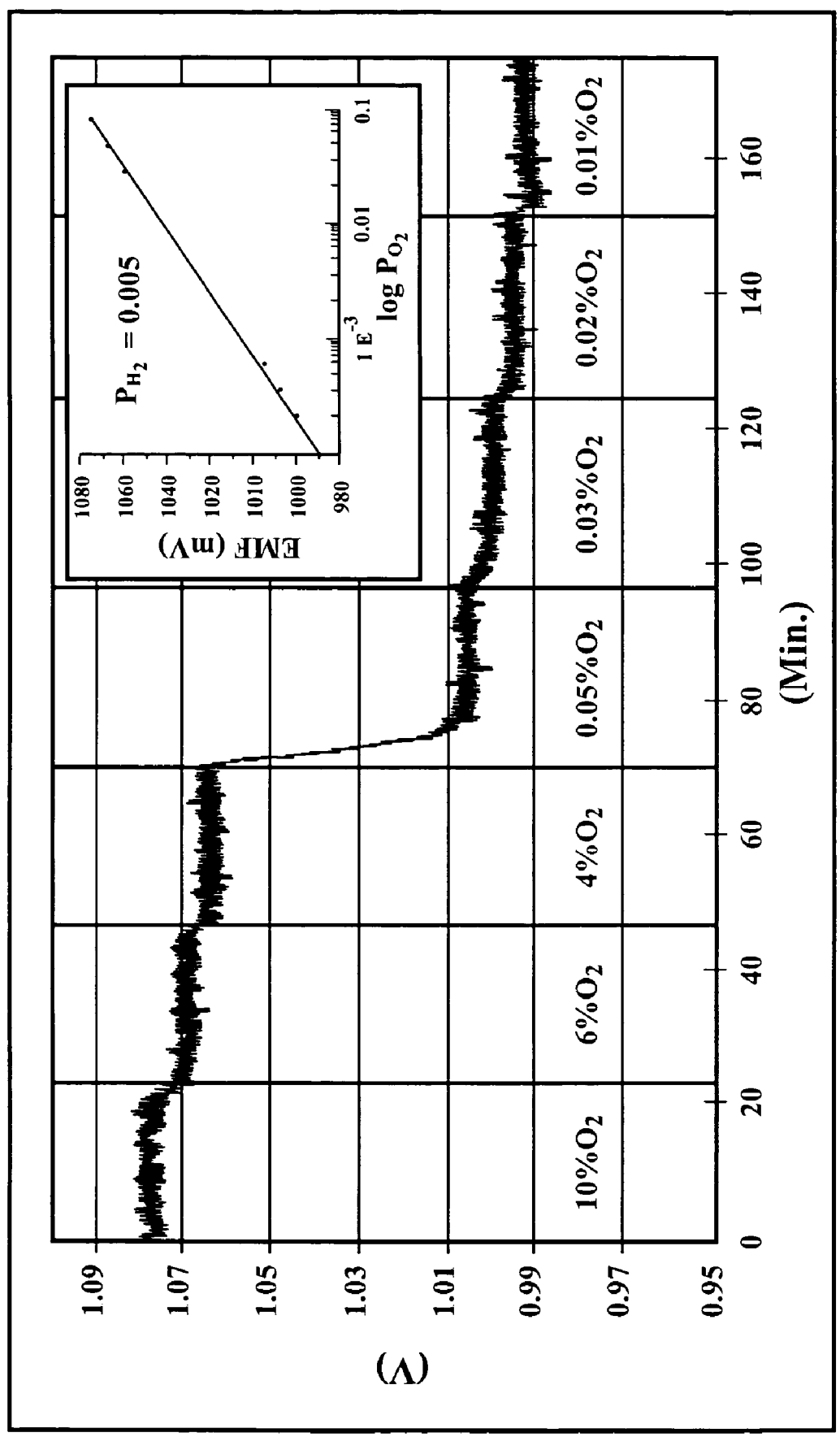
FIG. 3 is a graph showing oxygen dependence of EMF for the hydrogen probe described in FIG. 1 at a constant hydrogen pressure of 5×10⁻⁴ atm.

$$E = t_H \frac{RT}{2F} \ln \frac{P_{H_2}^2}{P_{H_2}^1} + t_O \frac{RT}{4F} \ln \frac{P_{O_2}^1}{P_{O_2}^2}$$ (Equation 1)

where $t_H$ and $t_O$ are the transference numbers of proton and oxygen ions in the electrolyte, respectively; and $P^1_{H2}$ and $P^1_{O2}$ are the equilibrium hydrogen and oxygen pressures generated by the solid-state reference mixture 4, respectively; and $P^2_{H2}$ and $P^2_{O2}$ are the respective values at the sensing electrode 3 in contact with molten aluminum. This shows the presence of oxygen conductivity in the proton conductor 1. The oxygen pressure dependence in the response of the hydrogen probe is shown in FIG. 3, where EMF changes as oxygen partial pressure changes for a constant hydrogen pressure of 5×10⁻⁴ atm.

The equilibrium hydrogen pressure $P^1_{H2}$ at the reference electrode 2 is thermo-chemically determined by the reaction 1 between metal (M) and metal hydride (MH₂) for a given temperature.

M+H₂=MH₂ (Reaction 1)

In order to determine the hydrogen pressure at the sensing electrode 3 $P^2_{H2}$, both the internal reference oxygen pressure $P^1_{O2}$ and the oxygen pressure at the outer sensing electrode 3 $P^2_{O2}$ have to be fixed. Both of the oxygen pressures can be also determined by the following reaction 2 between metal and metal oxide to fix the oxygen partial pressure.

$$M_x + \frac{y}{2}O_2 = M_xO_y$$ (Equation 2)

By measuring the EMF of the cell, we can obtain the dissolved hydrogen content in liquid aluminum $P^2_{H2}$ from Equation 1 by substituting the known values of $t_H$, $t_O$, $P^1_{H2}$, $P^1_{O2}$ and $P^2_{O2}$.

Figure 2:
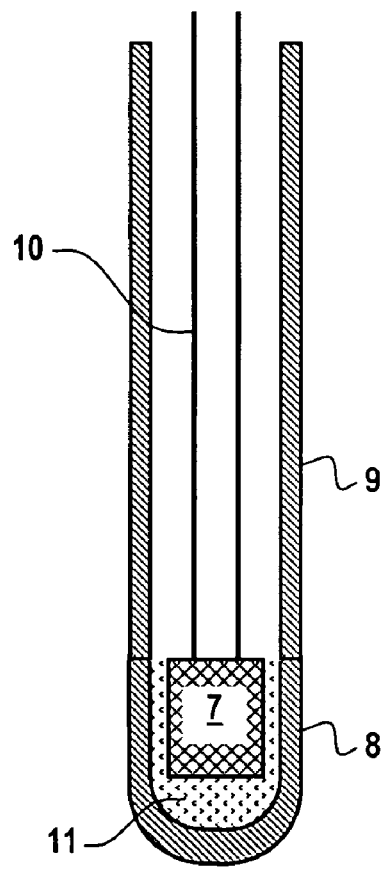
FIG. 2 is a schematic drawing illustrating the structure of a hydrogen probe according to an embodiment of the present invention.

FIG. 2 is a schematic drawing illustrating a structure of a hydrogen probe where the sensing unit of FIG. 1 has been inserted in a tube type support. The sensing unit 7 depicted in FIG. 1 resides in a ceramic tube 9 made of, for example, alumina, graphite, mullite or silicon nitride and sealed gas-tight with a ceramic adhesive, and is electrically connected to a controller (not shown) via electrical lead wires 10 (similar function as the pt wires 6 in FIG. 1) having a diameter less than 200 μm. A diameter of the electrical lead wires is chosen such that the sensing unit 7 maintains a gas-tight seal. A protection cover 8 such as porous graphite and porous alumina is adopted to protect the sensing unit 7 from a direct contact with reactive molten aluminum. The protection cover 8 functions as a physical filter so that the molten aluminum cannot penetrate through the protection cover 8, while hydrogen gas can easily pass through it. In order to fix the oxygen pressure at the outer sensing electrode 3 for a stable output, a stabilizing powder 11 such as a mixture of metal (Ti, Zr, Ca, Mn, FeO, or Ni) and metal oxide powder or carbon powder is filled in between the sensing unit 7 and the protection cover 8. The stabilizing powder 11 acts as a stabilizing agent. For example, graphite produces an equilibrium ratio of CO and $CO_2$ concentration of gases according to the following reaction 3.

C+CO₂=2CO (Reaction 3)

The reaction 3 subsequently produces a corresponding oxygen partial pressure by the following reaction 4.

$2CO_2 = 2CO + O_2$ (Reaction 4)

Figure 4:
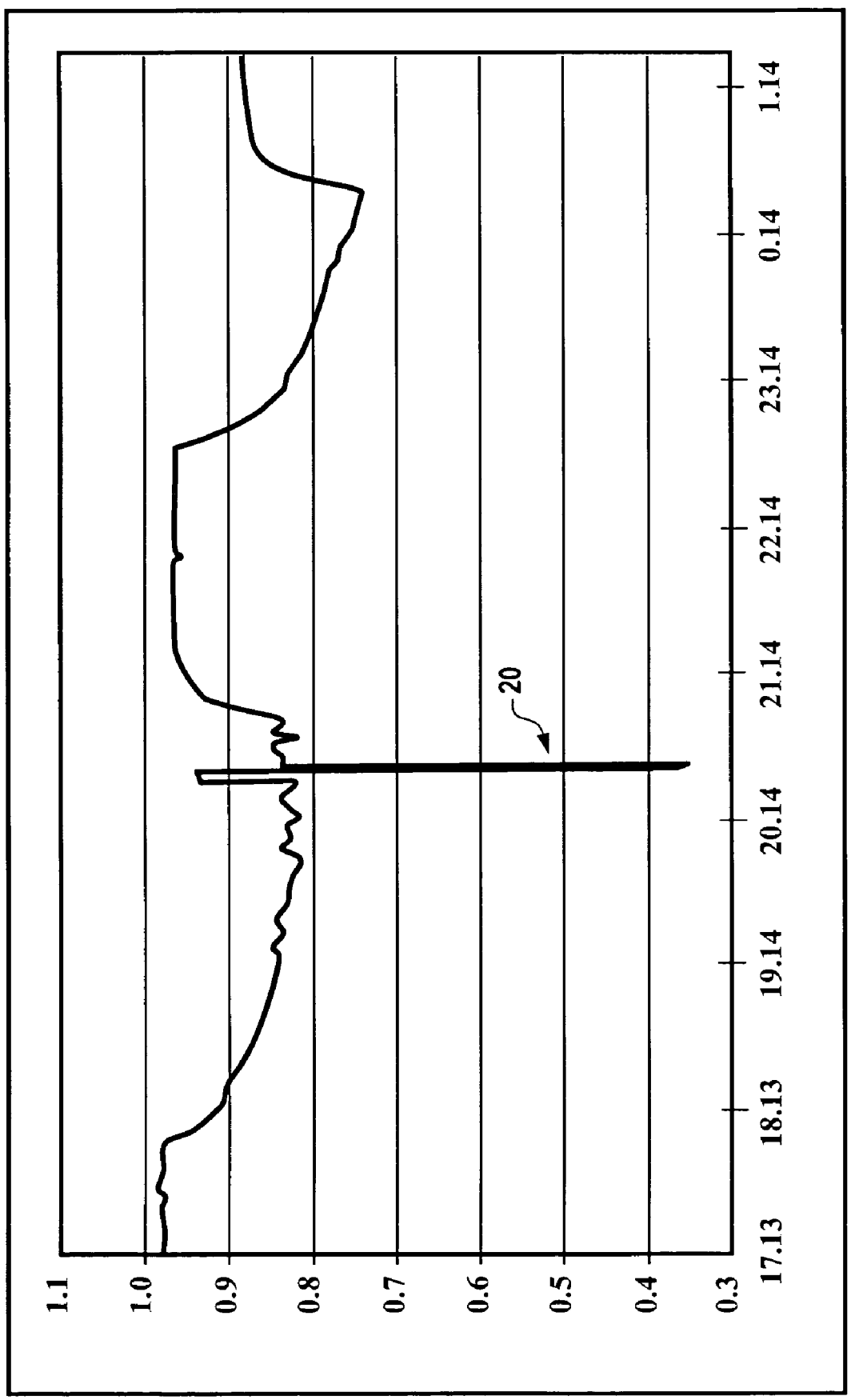
FIG. 4 is a graph showing a transient in EMF measured by a hydrogen probe without a stabilizing powder, as an ambient gas changes from 10% $H_2$ to Ar in molten aluminum.

Without the stabilizing powder 11, EMF may vary abruptly when the hydrogen probe moves in the molten aluminum, as shown in FIG. 4. However, when the stabilizing powder 11 is added between the sensing unit and the protection cover 8, such an abrupt change in EMF, as illustrated by transient 20 in FIG. 4, does not occur during the measurement.

In sum, the use of a solid-state reference in an electrochemical probe has raised such problems as instability of EMF and long-term instability. The present invention, however, provides a hydrogen probe with improved EMF stability, as well as a packaging method for the hydrogen probe for long-term stability. In addition, the principles of the present invention allow the structure of the measuring device to remain simple, which in turn provides convenience and low cost of measurements.

It will be apart to those skilled in the art that various modifications and variation can be made in the present invention without departing from the spirit or scope of the invention. Thus, it is intended that the present invention cover the modifications and variations of this invention provided they come within the scope of the appended claims and their equivalents.

What is claimed is:

1. An electrochemical gas probe for measuring an amount of gas in a molten metal comprising:
   a sensing unit having a reference electrode, a sensing electrode, a solid-state reference mixture adjacent to the reference electrode, and a conductor between the reference electrode and the sensing electrode; and
   a supporting unit having a main support, a protection cover and a stabilizing material,
   wherein the stabilizing material is between the sensing unit and the protection cover of the supporting unit, and wherein the solid-state reference mixture includes a metal, a hydride of the metal, and an oxide of the metal.

2. The electrochemical gas probe according to claim 1, wherein the main support includes ceramic.

3. The electrochemical gas probe according to claim 2, wherein the main support and the protection covers are formed of the same material and as one body.

4. The electrochemical gas probe according to claim 1, wherein the main support includes graphite and is electrically grounded.

5. The electrochemical gas probe according to claim 1, wherein the sensing unit further includes an electrical lead wire for electrical connection to a controller, the electrical lead wire having a diameter less than 200 µm.

6. The electrochemical gas probe according to claim 1, wherein the metal includes one of Ti, Zr, and Ca.

7. The electrochemical gas probe according to claim 1, wherein the conductor is a proton conductor and includes calcium zirconate doped with indium.

8. The electrochemical gas probe according to claim 1, wherein the stabilizing material includes a mixture of a metal and an oxide of the metal.

9. The electrochemical gas probe according to claim 8, wherein the metal includes one of Ti, Zr, Ca, Mn, Fe, and Ni.

10. The electrochemical gas probe according to claim 1, wherein the sensing electrode is in contact with a carbon powder.

11. The electrochemical gas probe according to claim 1, wherein the sensing unit further includes a gas-tight ceramic lid for protecting the solid-state reference mixture.

12. The electrochemical gas probe according to claim 1, wherein the molten metal is either aluminum or zinc.

13. The electrochemical gas probe according to claim 1, wherein the sensing unit and supporting unit are physically and electrically separatable.

* * * * *